United States Patent
Grevalcuore et al.

(10) Patent No.: US 10,456,341 B2
(45) Date of Patent: Oct. 29, 2019

(54) COMPOSITIONS AND METHODS FOR SIMULTANEOUS RESHAPING AND DIRECT COLORING OF HAIR

(71) Applicant: ALFA PARF GROUP S.P.A., Bologna (IT)

(72) Inventors: Katiuscia Grevalcuore, Bergamo (IT); Antonio Consoli, Urgnano (IT); Otto Goettel, Marly (CH); Gianluca Borgnini, Carvico (IT)

(73) Assignee: ALFA PARF GROUP S.P.A., Bologna (IT)

( * ) Notice: Subject to any disclaimer, the term of this patent is extended or adjusted under 35 U.S.C. 154(b) by 97 days.

(21) Appl. No.: 15/102,924

(22) PCT Filed: Dec. 11, 2014

(86) PCT No.: PCT/EP2014/077346
§ 371 (c)(1),
(2) Date: Jun. 9, 2016

(87) PCT Pub. No.: WO2015/086734
PCT Pub. Date: Jun. 18, 2015

(65) Prior Publication Data
US 2016/0303014 A1    Oct. 20, 2016

(30) Foreign Application Priority Data

Dec. 13, 2013  (EP) .................................. 13197281

(51) Int. Cl.
| | | |
|---|---|---|
| *A45D 2/00* | (2006.01) |
| *A45D 7/00* | (2006.01) |
| *A45D 7/04* | (2006.01) |
| *A61K 8/44* | (2006.01) |
| *A61Q 5/04* | (2006.01) |
| *A61Q 5/06* | (2006.01) |
| *A61K 8/365* | (2006.01) |

(52) U.S. Cl.
CPC .............. *A61K 8/365* (2013.01); *A45D 2/001* (2013.01); *A45D 7/04* (2013.01); *A61K 8/44* (2013.01); *A61K 8/447* (2013.01); *A61Q 5/04* (2013.01); *A61Q 5/065* (2013.01); *A45D 2007/001* (2013.01); *A61K 2800/432* (2013.01); *A61K 2800/5922* (2013.01); *A61K 2800/882* (2013.01)

(58) Field of Classification Search
None
See application file for complete search history.

(56) References Cited

U.S. PATENT DOCUMENTS

| | | | |
|---|---|---|---|
| 6,945,254 B2 | 9/2005 | Schonert et al. | |
| 2002/0192175 A1 | 12/2002 | Patel et al. | |
| 2009/0041683 A1* | 2/2009 | Molenda | A61K 8/585 424/47 |
| 2016/0058683 A1* | 3/2016 | Engrassi | A61K 8/36 132/206 |

FOREIGN PATENT DOCUMENTS

| | | |
|---|---|---|
| DE | 19859722 A1 | 6/2000 |
| EP | 1797865 A2 | 6/2007 |
| EP | 2258337 A1 | 12/2010 |

OTHER PUBLICATIONS

International Search Report and Written Opinion of PCT/EP2014/077346 dated Mar. 13, 2015.

* cited by examiner

*Primary Examiner* — David J Blanchard
*Assistant Examiner* — Sarah J Chickos
(74) *Attorney, Agent, or Firm* — Silvia Salvadori, P.C.; Silvia Salvadori

(57) ABSTRACT

The invention concerns ready to use compositions for the reshaping and direct coloring of hair comprising glyoxylic acid, a glyoxyloyl amino acid or a mixture thereof and a direct dye, and a method for reshaping and coloring of hair by means of said compositions.

15 Claims, No Drawings

COMPOSITIONS AND METHODS FOR SIMULTANEOUS RESHAPING AND DIRECT COLORING OF HAIR

This application is a U.S. national stage of PCT/EP2014/077346 filed on 11 Dec. 2014, which claims priority to and the benefit of European Application No. 13197281.2 filed on 13 Dec. 2013, the contents of which are incorporated herein by reference in their entireties.

The invention concerns ready to use compositions for the reshaping and direct coloring of hair comprising glyoxylic acid or a derivative thereof and a direct dye. The invention also concerns a method for reshaping and coloring of hair by means of said compositions.

BACKGROUND OF THE INVENTION

The hair cosmetic industry offers a great diversity of products targeting the beautification of hair. Care products have become part of our everyday life. Besides treatments at home which commonly comprise shampooing and styling, coloration of hair and also reshaping have become the most important treatments in hairdresser's salons. In European countries the focus has been on permanent waving, whereas in American countries, mainly in Latin American countries, people often have very curly or frizzy hair which is hardly manageable hair straighteners stand out with a high demand by customers aiming at beauty, social acceptance and ease of daily hair maintenance.

The market has therefore offered various products for reshaping hair, either from straight hair into curly or wavy hair, or from frizzy or curly hair into straight hair which is also known as smoothing of hair.

One of the most important problems is that, although active ingredients are able to straighten wavy, curly or frizzy hair, said substances are often impaired by unfavorable safety profiles and high aggressiveness for hair.

Over the years three methods have been established for reshaping hair.

In the first two cases described below, a significant percentage of cystine disulfide bonds have to be disrupted. While there are other types of bonds between the polypeptides in hair fibers, such as ionic bonds, the permanent shape of the hair is essentially dependent on the disulfide bonds of cystine units. The chemical disruption of disulfide bonds is generally combined with mechanical straightening of the hair, such as combing. Straightening generally occurs due to changes in the relative positions of neighboring polypeptide chains within the hair fiber.

Method 1: Use of Reducing Agents

One method for chemical straightening of hair is substantially identical with the technique used in permanent waving. Relaxing is based on the chemical reduction of the cystine structure into two cysteine units followed by reconfiguration of the hair and restoring of cystine structures.

In general, the sulfur to sulfur cystine bonds in human hair maintain the hair in a naturally straight or curly configuration. Polypeptide chains are crosslinked by sulfur to sulfur bonds in cystine units. In order to permanently reshape the hair into a different configuration, a significant amount of the disulfide bonds (—S—S—) must be broken to form two (—SH) groups. Protein chains of the hair are locally disconnected from each other and the hair can now be reshaped. After the hair is reconfigured in a desired position, new disulfide bonds are reestablished, e.g. by the application of a hydrogen peroxide composition. The formation of the newly formed linking (—S—S—) groups leads to a longer lasting straightening effect. The commonly used active ingredient which is used for breaking the disulfide bonds is ammonium thioglycolate.

In more ancient times hydrogensulfite solutions and/or sulfite solutions and/or disulfite solutions were used to cleave disulfide bridges into a thiol group and a Bunte salt moiety; this method was found by Clark and Speakman in 1932 (see: W. Umbach: Kosmetik—Entwicklung, Herstellung and Anwendung kosmetischer Mittel, 2nd edition, Georg Thieme Verlag, Stuttgart, 1995).

Reducing compositions which contain higher amounts of hydrogensulfite, sulfite or disulfite do not have the strong intrinsic odor of compositions which comprise mercaptans. Fixing is carried out with the help of heat or by an oxidizing agent with the formation of new disulfide bridges, whereby the Bunte salt moieties are not available for fixing in the course of the treatment for reshaping. However, the degree of hair damage was high and the hair quality was considerably suffering. For these reasons and also for safety reasons this method was no longer applied.

One of the disadvantages of reducing agents is in the subsequent use of an oxidizing neutralizer, such as hydrogen peroxide, to chemically relink the hair keratin disulfide bonds and also deactivate the reducing agent. As reducing compounds are usually buffered in an alkaline state, any excess of hydrogen peroxide must be removed at the same time to avoid stronger lightening or discoloration of the hair. Discoloration is often observed if dyed hair is treated with compositions containing thioglycolate.

The inconveniences of the use of reducing agents which are able to break-off the disulfide bonds is the pungent odor of the thio compounds, mainly the strong smell of ammonium thioglycolate.

Method 2: Use of Alkali Agents

For many years solutions of alkali hydroxides have been used which efficiently straighten hair. Sodium hydroxide is commonly used in chemical relaxers and provides long lasting effects. Alkali metal hydroxides are key ingredients in products that are referred to as "lye" relaxers.

In U.S. Pat. No. 4,304,244 guanidine hydroxide was claimed as another common option of relaxer chemical; relaxers containing this compound are also referred to as "no-lye" relaxers. However, the strength of both relaxer types varies from a pH of 12 to 14.

Hair treatments with a formulation containing hydroxide based relaxers include two consecutive chemical steps. In the first step the treatment leads to the cleavage of cystine (—S—S—) bridges whereby a cysteine moiety and a dehydroalanine moiety are formed. According to C. Zviak, The Science of Hair Care, pp. 185-186 (1986) one sulfur atom is removed from the hair and converted into a HOS$^-$ ion. In this situation important parts of the polypeptide chains are not crosslinked and the hair can be reshaped. In the second step the cysteine thiol group reacts with the double bond of the dehydroalanine moiety to form a lanthionine bridge (—CH$_2$—S—CH$_2$—) which largely restores mechanical stability of the hair.

Treatments with hydroxides, in particular with alkali hydroxides, are very effective in producing stable, but lead to completely irreversible, crosslinks in the treated hair so that subsequent reshaping of the hair is excluded. In addition, the applied chemical compositions are very harsh to both the scalp and the hair and the use of such compositions has resulted in numerous instances of scalp irritation and burning, in substantial reduction of the strength of treated hair and in some cases to considerable hair loss as disclosed in Int. J. of Cosmetic Science, 2014, (36), 2-11.

Prolonged exposure of hair to such a strong alkali can even dissolve the hair. Various attempts have therefore been made to replace the strong alkali metal hydroxides by less active hydroxides. However, these compositions are not satisfactory, neither in terms of relaxing nor in cosmetic terms.

The aforementioned straightening systems which are all based on breaking off the cystine bridges have a deteriorating effect on the hair.

Another approach for reshaping hair is the introduction of crosslinks caused by aldehydes.

Method 3: Use of Formaldehyde

U.S. Pat. No. 2,390,073 claimed a hair treatment system based on formaldehyde or a formaldehyde releasing compound. According to said document, formaldehyde should establish new crosslinks in the polypeptide structures which overcompensate the forces of the natural cystine bonds and provide the straightening effect. Typical concentrations of formaldehyde in such straighteners were between 5 and 10 percent. Later-on formaldehyde adducts have been commercialized in various straightener compositions until the use of formaldehyde was restricted to concentrations of 0.2% maximum for safety and regulation observance. Considerable amounts of formaldehyde based straightener compositions present at 5 to 10% by weight evaporate in the course of the hair treatment since the processes require blow dryer or hot flat iron treatments that causes the product to steam. In consideration of the toxicological profile of formaldehyde and its adducts it was finally concluded that there is no safe level of formaldehyde assessment for this product.

US20130118520 discloses that human hair can also be straightened by the use of higher amounts of glyoxylic acid at increased temperatures, e.g. by means of a shaping iron.

However, the use of glyoxylic acid at higher temperatures frequently leads to lightening of hair, in particular of artificially colored hair, which gave reason for dissatisfaction. The use of glyoxylic acid as substitute of formaldehyde in semi-permanent hair straightening has been thoroughly discussed in Int. J. of Cosmetic Science, 2014, (36), 459-470.

It is evident that straightening or relaxing the curls of very curly hair improves the manageability and ease of styling such hair, independently of the applied techniques and compositions described above. Currently there is a strongly increasing demand for the hair care products referred to as "smoothing agents", "straighteners" or "hair relaxers," which can reshape naturally curly hair.

Various techniques for waving or straightening hair have been applied which are based on chemical methods, physical methods and also a combination of both.

In particular if glyoxylic acid is used for straightening hair where lightening occurs it is customary to perform a two-step process where the hair is smoothed in the first step, then tinted with a color in another step to recover the previous hair color. However, two subsequent hair treatments are hair damaging and laborious.

DE19859722 discloses colorants, mainly oxidative colorants, comprising lower amounts of oxocarboxylic acids and derivatives thereof which should intensify the hair color under standard processing conditions. The disclosed compositions are not suitable for straightening and coloring hair in one step. Moreover, only oxidative dyes may be used.

EP 1326579 uses short chained carboxylic acids for stabilizing color results.

EP 2258337 discloses cleansing and conditioning compositions comprising direct dyes and glyoxylic acid in concentrations insufficient to provide semipermanent straightening effect. US 2002/192175 discloses straightening compositions comprising alkaline agents and cationic dyes causing an irreversible straightening since the alkaline agents break down the disulfide bridges of the keratin fibers with consequent breaking of the hair and irritation of the scalp.

DESCRIPTION OF THE INVENTION

It has been surprisingly found that compositions comprising components of formula (I) or (II) and at least one suitable direct dye are able to straighten and color keratinous fibers, especially human hair, in an outstanding manner. The hair is then well reshaped and evenly colored.

The compositions according to the invention enable the contemporaneous reshaping and coloring of the hair. The compositions of the invention are advantageous particularly with respect to those disclosed in DE 19859722 since different kinds of dyes (e.g. acid direct dyes, basic direct dyes and disperse neutral hair dyes), may be used, being compatible with the formulation system.

The present invention accordingly provides aqueous preparations for simultaneous reshaping and dyeing of keratinous fibers comprising at least one direct dye and a component represented by structure (I) or the corresponding monohydrate represented by structure (II), respectively,

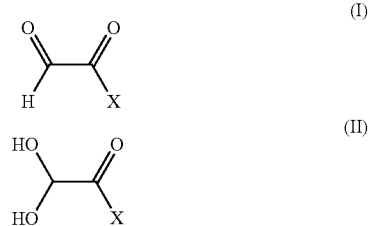

wherein the group X is either a hydroxy group, or X is a —NHR group wherein R represents an amino acid radical and the N atom is the amino group of the corresponding amino acid, said compounds of formula I or II being present in a concentration from 5.5 to 25% by weight.

Said derivatives of glyoxylic acid with amino acids which have a carbonamide structure are generally called glyoxyloyl amino acids. Suitable amino acids to form a derivative with glyoxylic acid are for instance glycine, alanine, arginine, valine, leucine, isoleucine, serine, threonine, lysine, histidine, aspartic acid, glutamic acid, cysteic acid, cystine or carbocysteine. Glyoxyloyl Carbocysteine is preferred.

Glyoxylic acid, a glyoxyloyl amino acid or a mixture thereof may be present, for example, in a concentration sufficient to effect relaxation of the keratinous fibers without damaging the fibers. The concentration ranges from 5.5% to 25% by weight relative to the total weight of the composition, preferably from 6% to 25% by weight, more preferably from 8 to 25%, even more preferably from 10 to 25%.

The compositions may further comprise one or more conventional ingredients such as thickeners, conditioning agents, opacifiers, hydrophilic solvents and care products. The compositions of the invention may also further comprise one or more auxiliary agents selected from anionic, non ionic or cationic surfactants, anionic, non ionic or cationic thickeners, organic solvents, silicones, cationic polymers.

The composition for simultaneous reshaping and coloring hair according to the invention can either be ready-to-use composition or it can be provided as a kit comprising a two agent type hair cosmetic which comprises a first agent containing glyoxylic acid or a glyoxyloyl amino acid and a second agent containing at least one dye. Prior to using, the first agent and the second agent are mixed to obtain the ready-to-use composition.

Another embodiment of the invention is therefore a kit wherein the composition comprising the reshaping agent and the composition comprising the dye are separated from each other.

The ready-to-use compositions can be in form of a liquid, a cream, a gel, or a foam.

The invention also provides a process for the reshaping and direct coloring of hair, comprising:

(i) contacting the hair with an aqueous ready-to-use composition of the invention containing glyoxylic acid or a glyoxyloyl amino acid and a dye, whereby the processing time is between 5 minutes and 45 minutes;

(ii) shaping the hair by means of heat and shaping aids.

The hair is preferably washed with a clarifying shampoo and blow-dried before being contacted with the ready-to-use composition of the invention.

Heat may be applied either by an helmet, blow-drier, plates or other conventional devices. Heat may be applied already in step (i).

Rinsing and drying of the hair is carried out either before or immediately after shaping.

An after-treatment product may then be applied on the hair.

According to a first embodiment, the process of the invention includes the following steps:

i) cleaning the hair by washing with a clarifying shampoo and blow-drying;

(ii) contacting the hair with an aqueous ready-to-use composition of the invention containing glyoxylic acid or a glyoxyloyl amino acid and a dye, whereby the processing time is between 5 minutes and 45 minutes, followed by combing and blow-drying (iii) optionally during the step (ii) use a source of heat different from a blow-dryer;

(iv) shaping the hair by means of heat and shaping aids;

(v) rinsing out the hair and drying;

(vi) optionally treating the hair with an after-treatment product.

According to a second embodiment, the process includes the following steps:

(i) cleaning the hair by washing with a clarifying shampoo and blow-drying;

(ii) contacting the hair with an aqueous ready-to-use composition of the invention containing glyoxylic acid or a glyoxyloyl amino acid and a dye, whereby the processing time is between 5 minutes and 45 minutes (iii) optionally during the step (ii) use a source of heat different from a blow-dryer;

(iv) rinse with tap water and dry;

(v) shaping the hair by means of heat and shaping aids;

(vi) optionally treating the hair with an after-treatment product.

According to the process of the invention, the composition is applied to the hair, tack-dried with a blow dryer, and left for approximately 5 to 45 minutes, preferably 15 to 45 minutes at ambient temperature. The coated hair is then treated with a flat iron with usually 10 cycles at temperatures above 100° C., preferably between 150° C. to 250° C.; most preferably between 200° C. and 220° C.

The process of the invention may optionally comprise pre-washing the hair and rinsing and drying steps before or after the shaping step (ii).

The invention provides a simultaneous hair reshaping and coloring method that is efficient, time-lasting, minimizing the damage to the hair and other secondary effects and inconveniences for the users with good visual results.

Dyes

Acidic dyes are normally ideally suited compounds for being used in strongly acidic direct dyeing compositions.

It was surprisingly found that numerous anionic dyes normally used in acidic direct dyeing systems are not necessarily useful in combination with glyoxylic acid and derivatives thereof. It has now been found that appropriate dyes can be selected not only from anionic dyes but also from cationic dyes, zwitterionic dyes, nonionic dyes or cationic dyes which may perform at the same level or even better than the aforementioned acidic dyes.

The composition of the invention may therefore comprise a single dye or a mixture of dyes whereas the dyes may consist of molecules of the same or a different ionogenic nature.

Dyes are selected from anionic, nonionic or cationic dyes

Anionic Dyes:

Suitable anionic dyes are for instance selected from Acid Black 1 (CI 20470); Acid Blue 1 (CI 42045); Food Blue 5 (CI 42051); Acid Blue 7 (CI 42080); Acid Blue 9 (CI 42090); Acid Blue 74 (CI 73015); Acid Red 18 (CI 16255); Acid Red 27 (CI 16185); Acid Red 33 (CI 17200); Acid Red 40 (CI 18070), Acid Red 52 (CI 45100), Acid Red 87 (CI 45380); Acid Red 92 (CI 45410); Acid Orange 7 (CI 15510); Acid Violet 43 (CI 60730); Acid Yellow 1 (CI 10316); Acid Yellow 3 (CI 47005); Acid Yellow 23 (CI 19140); Food Yellow 8 (CI 14270), Acid Green 25, D&C Black No. 2, D&C Black No. 3, FD&C Blue No. 1, D&C Blue No. 4, D&C Brown No. 1, FD&C Green No. 3, D&C Green No. 6, D&C Green No. 8, D&C Orange No. 4, D&C Orange No. 5, D&C Orange No. 10, D&C Orange No. 11, FD&C Red No. 4, D&C Red No. 6, D&C Red No. 7, D&C Red No. 17, D&C Red No. 21, D&C Red No. 27, D&C Red No. 30, D&C Red No. 31, D&C Red No. 34, D&C Red No. 36, FD&C Red No. 40, D&C Violet No. 2, FD&C Yellow No. 6, D&C Yellow No. 7, D&C Yellow No. 8, D&C Yellow No. 11.

Preferred dyes include Acid Yellow 1, Acid Yellow 3, Acid Yellow 23, Acid Orange 7, Acid Red 33, Acid Red 40, Acid Red 52, Acid Red 92, Acid Violet 43, Acid Blue 7 and Acid Blue 9.

Nonionic Dyes:

Suitable nonionic dyes are for instance of the nitrobenzene type and are selected from 2-Amino-3-nitrophenol; 2-[(2-Hydroxyethyl)amino]-1-methoxy-5-nitrobenzene; 1-(2-Hydroxyethoxy)-3-methylamino-4-nitrobenzene; 2,3-(Dihydroxypropoxy)-3-methylamino-4-nitrobenzene; 1-[(2-Ureidoethyl)amino]-4-nitrobenzene; 4-[(2-Hydroxyethyl)amino]-3-nitro-1-methylbenzene; 1-[(2-Hydroxyethyl)amino]-2-nitrobenzene (HC Yellow No. 2); 1-(2-Hydroxyethoxy)-2-[(2-hydroxyethyl)amino]-5-nitrobenzene (HC Yellow No. 4); 1-Amino-2-[(2-hydroxyethyl)amino]-5-nitrobenzene (HC Yellow No. 5); 4-[(2,3-Dihydroxypropyl)amino]-3-nitro-1-trifluoromethylbenzene (HC Yellow No. 6); 1-(4-Aminophenylazo)-2-methyl-4-(bis-2-hydroxyethyl)aminobenzene (HC Yellow No. 7); 3-[(2-Aminoethyl)amino]-1-methoxy-4-nitrobenzene hydrochloride (HC Yellow No. 9); 1-Chloro-2,4-bis-[(2-hydroxyethyl)amino]-5-nitrobenzene (HC Yellow No. 10); 2-[(2-Hydroxyethyl)amino]-5-nitrophenol (HC Yellow No. 11); 1-Chloro-4-[(2-hydroxyethyl)amino]-3-nitrobenzene (HC Yellow No. 12); 4-[(2-Hydroxyethyl)amino]-3-nitro-1-trifluoromethyl-benzene (HC Yellow No. 13); 4-[(2-Hydroxyethyl)amino]-3-nitro-benzonitrile (HC Yellow No. 14); 4-[(2-Hydroxyethyl)amino]-3-nitro-benzamide (HC Yellow No. 15); 1,4-diamino-2-nitrobenzene; 1,4-Bis[(2-hydroxyethyl)amino]-2-nitrobenzene; 2-Amino-4,6-dinitrophenol; 4-Amino-3-nitrophenol; 1-Amino-5-chloro-4-[(2-hydroxyethyl)amino]-2-nitrobenzene; 4-[(2-Hydroxyethyl)amino]-3-nitrophenol; 4-[(2-Nitrophenyl)amino]phenol (HC Orange No. 1); 1-[(2-Aminoethyl)amino]-4-(2-hydroxyethoxy)-2-nitrobenzene (HC Orange No. 2); 4-(2,3-Dihydroxypropoxy)-1-[(2-hydroxyethyl)amino]-2-nitrobenzene (HC Orange No. 3); 2-[(2-Hydroxyethyl)amino]-4,6-dinitro-phenol; 4-Ethylamino-3-nitrobenzoic acid; 2-[(4-Amino-2-nitrophenyl)amino]-benzoic acid; 2-Chloro-6-ethylamino-4-nitrophenol; 2-Amino-6-chloro-4-nitrophenol; 4-Nitro-o-phenylenediamine; 4-[(3-Hydroxypropyl)amino]-3-nitrophenol; 2,5-Diamino-6-nitropyridine; 1,2,3,4-Tetrahydro-6-nitroquinoxaline; 4-Amino-2-nitro-diphenylamine (HC Red No. 1); 4-Amino-1-[(2-hydroxyethyl)amino]-2-nitrobenzene (HC Red No. 3); 1-Amino-4-[(2-hydroxyethyl)amino]-2-nitrobenzene (HC Red No. 7); 1-Amino-5-chloro-4-[(2,3-dihydroxypropyl)amino]-2-nitrobenzene (HC Red No. 10); 5-Chloro-1,4-[di(2,3-dihydroxypropyl)amino]-2-nitrobenzene (HC Red No. 11); 1-Amino-4-[di(2-hydroxyethyl)amino]-2-nitrobenzene hydrochloride (HC Red No. 13); 7-Amino-3,4-dihydro-6-nitro-2H-1,4-benzoxazine (HC Red No. 14); 1-Amino-3-methyl-4-[(2-hydroxyethyl)amino]-6-nitrobenzene (HC Violet No. 1); 1-(3-Hydroxypropylamino)-4-[di(2-hydroxyethyl)amino]-2-nitrobenzene (HC Violet No. 2); 1-(2-Hydroxyethyl)amino-2-nitro-4-[di(2-hydroxyethyl)amino]-benzene (HC Blue No. 2); 1-Methylamino-4-[methyl-(2,3-dihydroxypropyl)amino]-2-nitrobenzene (HC Blue No. 6); 1-[(2,3-Dihydroxypropyl)amino]-4-[ethyl-(2-hydroxyethyl)amino]-2-nitrobenzene hydrochloride (HC Blue No. 9); 1-[(2,3-Dihydroxypropyl)amino]-4-[methyl-(2-hydroxyethyl)amino]-2-nitrobenzene (HC Blue No. 10); 4-[Di(2-hydroxyethyl)amino]-1-[(2-methoxyethyl)amino]-2-nitrobenzene (HC Blue No. 11); 4-[Ethyl-(2-hydroxyethyl)amino]-1-[(2-hydroxyethyl)amino]-2-nitrobenzene hydrochloride (HC Blue No. 12); 2-((4-Amino-2-nitrophenyl)amino)-5-dimethylaminobenzoic acid (HC Blue No. 13);

disperse dyes may also be used, for instance Disperse Black 9, Disperse Red 17, Disperse Violet 1, Disperse Violet 4, Disperse Violet 15, Disperse Violet 27, Disperse Blue 1, Disperse Blue 3, Disperse Blue 7, Disperse Blue 72, and Disperse Blue 377, 2-Hydroxyethyl picramic acid, 4-Nitrophenyl aminoethylurea, 3-Methylamino-4-nitrophenoxyethanol, 2-Nitro-5-glyceryl methylaniline.

Preferred are HC Yellow No. 7, 2-Amino-6-chloro-4-nitrophenol, 4-Nitro-o-phenylenediamine, 4-Amino-3-nitrophenol, HC Orange No. 1, HC Red No. 1, HC Red No. 3, HC Red No. 13, Disperse Violet 1, HC Yellow No. 13, and Disperse Red 17.

Cationic Dyes:

Suitable cationic dyes are selected from Basic Yellow 57, Basic Yellow 87, Basic Brown 16, Basic Brown 17, Basic Orange 31, Basic Orange 69, Basic Red 51, Basic Red 76, Basic Blue 124, Hydroxyanthraquinone aminopropyl methyl morpholinium methosulfate as well as HC Blue 15, HC Blue 16 and HC Blue 17, preferably Basic Yellow 57, Basic Yellow 87, Basic Brown 16, Basic Brown 17, Basic Orange 31, Basic Red 51, Basic Red 76, HC Blue 15 and HC Blue 16.

Preferred cationic dyes include Basic Yellow 57, Basic Yellow 87, Basic Brown 16, Basic Brown 17, Basic Orange 31, Basic Red 51, Basic Red 76, HC Blue 15 and HC Blue 16, Basic blue 75.

The total amount of one or more dyes present in the ready-to-use composition is between 0.01% and 5.0% by weight.

Auxiliary Agents

The invention provides a composition comprising, besides glyoxylic acid and one or more dyes, a combination of components selected from hydrophilic organic solvents, wax components, surfactants, water soluble polymers and thickeners, silicones, fatty oils, opacifiers and opacifiers which have a viscosity controlling function, quaternary viscosity controlling agents, protein hydrolyzates, complexing agents, and preservatives.

Suitable organic solvents are water soluble such as glycols, glycol ethers and polyols containing 2 to 6 carbon atoms. Accordingly, suitable glycols are ethylene glycol, propanediols and butanediols. Suitable glycol ethers are, for example, ethyl glycol, ethyl diglycol, diethylene glycol, triethylene glycol and dipropylene glycol. Suitable polyols are, for example, glycerol, erythritol, pentaerythritol, trimethylol propane, diglycerol and sorbitol. Examples of the alkylene carbonates include ethylene carbonate and propylene carbonate.

Suitable polyalkylene glycols are, for example, the liquid polyethylene glycols, the polypropylene glycols and the addition products of ethylene oxide onto propylene glycol or onto polypropylene glycols with molecular weights of up to 1,000 D.

The organic solvents may be present in the ready-to-use composition in a wide range of up to about 50% by weight.

Suitable wax components are selected from fatty alcohols containing 10 to 30 carbon atoms, such as capric alcohol, lauryl alcohol, myristyl alcohol, cetyl alcohol, stearyl alcohol, behenyl alcohol.

Suitable nonionic surfactants are surfactants which contain a lipophilic, preferably linear C8-22 alkyl or acyl group and, as a hydrophilic group, a glucoside or polyglucoside group, a glycerol or polyglycerol group, a sorbitan group or a polyglycol ether group or several of these groups. Suitable nonionic surfactants are above all those which are available in water-free form, for example products of the addition of ethylene oxide onto fatty alcohols, fatty acids, fatty acid mono- or diglycerides, onto fatty acid alkanolamides, onto sorbitan fatty acid esters, onto methyl glucoside fatty acid esters or onto alkyl glucosides. Examples of suitable nonionic surfactants are ethoxylated fatty alcohols such as ceteareth-22, ceteareth-25, ceteareth 50 and steareth-20, steareth-21 and steareth-100. PEG-15 Cocopolyamine having antistatic properties may also be used.

Another particularly suitable group of nonionic surfactants includes the silicone copolyols marketed, for example, under the name of Dow Corning Surfactant (Dow Corning) or Abil (Goldschmidt).

Suitable anionic surfactants are any surfactant characterized by a preferably linear aliphatic backbone structure containing up to 56 carbon atoms which is linked to a sulfate, sulfonate, phosphate or carboxylate group. Particularly suitable anionic surfactants are foaming types such as, for example, alkyl sulfates, alkanesulfonates, α-olefin sulfonates, acyl isethionates, acyl taurides, acyl sarcosides, sulfosuccinic acid monoalkyl ester salts and alkyl polyglycol ether carboxylates in the form of their alkali metal, magnesium, ammonium or alkanolammonium salts. Anionic surfactants obtainable in water-free fine-particle form are preferably used. Examples of said surfactants include Oleth-5 Phosphate, Ceteth-10 Phosphate, Ceteth-20 Phosphate as well as the bifunctional Dioleyl Phosphate and Dicetyl Phosphate (INCI names).

Suitable zwitterionic surfactants are betaine surfactants, for example C12-18 alkyl dimethyl acetobetaine, cocoamidopropyl dimethyl acetobetaine, imidazolinium betaines and sulfobetaines containing a preferably linear C10-18 alkyl or acyl group. Particularly suitable betaine surfactants are those obtainable in water-free, fine-particle form. A particularly suitable product is, for example, the cocoamidopropyl betaine marketed as Tego Betain CKD (N—N-dimethyl-N-lauroylamidopropyl)-ammoniumacetobetaine).

Ampholytic surfactants are surfactants which, besides a preferably linear C8-18 alkyl or acyl group, contain a protonatable amino group and a carboxyl group and are capable of forming inner salts. Suitable ampholytic surfactants are, for example, N—(C12-18)-alkyl-N-methyl glycine, N—(C12-18)-acylaminopropyl-N-methyl glycine, N—(C12-18)-acylaminoethyl-N-methyl glycine, N—(C12-18)-acylaminopropyl-N-hydroxyethyl glycine, 2-(C12-18)-alkyl carboxymethyl-3-hydroxyethyl imidazoline and 2-N—(C8-18)-alkylaminoethanecarboxylic acid.

Suitable cationic surfactants are, for example, quaternary ammonium salts, such as di(C10-C24)-alkyldimethylammonium chloride or bromide, preferably di(C12-C18)-alkyldimethylammonium chloride or bromide; (C10-C24)-alkyldimethylethylammonium chloride or bromide; (C10-C24)-alkyltrimethylammonium chloride or bromide, preferably cetyltrimethylammonium chloride or bromide and (C20-C22)-alkyltrimethylammonium chloride or bromide; (C10-C24) alkyldimethylbenzylammonium chloride or bromide, preferably (C12-C18)-alkyldimethylbenzylammonium chloride; N—(C10-C18)-alkylpyridinium chloride or bromide, preferably N—(C12-C16)-alkylpyridinium chloride or bromide; N—(C10-C18)-alkylisoquinolinium chloride, bromide or monoalkyl sulfate; N—(C12-C18)-alkylpolyoylaminoformylmethylpyridinium chloride; N—(C12-C18)-alkyl-N-methylmorpholinium chloride, bromide or monoalkyl sulfate; N—(C12-C18)-alkyl-N-ethylmorpholinium chloride, bromide or monoalkyl sulfate; (C16-C18)-alkylpentaoxyethylammonium chloride; diisobutylphenoxyethoxyethyldimethylbenzylammonium chloride; salts of N,N-diethylaminoethylstearylamide and -oleylamide with hydrochloric acid, acetic acid, lactic acid, citric acid, phosphoric acid; N-acylaminoethyl-N,N-diethyl-N-methylammonium chloride, bromide or monoalkyl sulfate and N-acylaminoethyl-N,N-diethyl-N-benzylammonium chloride, bromide or monoalkyl sulfate, where acyl is preferably stearyl or oleyl.

Cetyltrimethylammonium chloride, cetylpyridinium chloride, benzalkonium chloride, benzethonium chloride, dimethyldioctadecylammonium chloride, dioctadecyldimethylammonium bromide as well as distearoylethyl dimonium chloride (DSEDC) are preferred.

Surfactants can be included in the composition in amounts from about 0.5% to 6.0% by weight, preferably from about 1.0% to 4% by weight.

The composition according to the invention can contain cationic polymers with the INCI name Polyquaternium, e.g. copolymers of vinylpyrrolidone/N-vinylimidazolium salts (products commercially available under the name "Luviquat®"), copolymers of N-vinylpyrrolidone/dimethylaminoethyl methacrylate, quaternized with diethylsulfate, copolymers of N-vinylcaprolactam/N-vinylpyrrolidone/N-vilylimidazolium salts; cationic cellulose derivatives (Polyquaternium-4 and -10), acrylamide/diallyldimethylammonium chloride copolymers (Polyquaternium-7). A particularly preferred cationic polymer, if crosslinking is desired, is the poly(methacryloyloxyethyltrimethylammonium chloride) with the INCI name Polyquaternium-37.

The preferred amount of such polymers may range from 0.1 to 5% by weight, preferably from 0.1 to 1.0% by weight.

The viscosity-increasing agent may be selected from the group consisting of non-ionic thickeners, cationic thickeners, anionic thickeners, amphoteric thickeners, and mixtures thereof; preferably non-ionic thickeners, anionic thickeners, and mixtures thereof.

Suitable anionic thickener polymers are Ammonium Acryloyldimethyltaurate/VP Copolymer, Ammonium Acryloyldimethyltaurate/Carboxyethyl Acrylate Crosspolymer, and Ammonium Acryloyldimethyltaurate/Beheneth-25 Methacrylate Crosspolymer.

As polymers from the group including celluloses, alginates and polysaccharides advantageously methyl celluloses, ethylcelluloses, hydroxyethylcelluloses, methylhydroxyethylcelluloses, methylhydroxypropylcelluloses, carboxymethylcelluloses, alginic acids, sodium alginate, ammonium alginate, calcium alginate, gum arabic, guar gum or xanthan gum, alone or in combination with each other can be used; Disteareth-100 IPDI (INCI name) is particularly suitable.

Suitable cationic thickeners are derivatives of Hydroxypropyl Guar, examples of which include polymers known via the INCI nomenclature as Guar Hydroxypropyltrimonium Chloride, such as the products sold under the name Catinal CG-100, Catinal CG-200 by the company Toho, Cosmedia Guar C-261N, Cosmedia Guar C-261N, Cosmedia Guar C-261N by the company Cognis, DiaGum P 5070 by the company Freedom Chemical Diamalt, N-Hance Cationic Guar by the company Hercules/Aqualon, Hi-Care 1000, Jaguar C-17, Jaguar C-2000, Jaguar C-13S, Jaguar C-14S, Jaguar Excel by the company Rhodia, Kiprogum CW, Kiprogum NGK by the company Nippon Starch.

Hydroxypropyl derivatives of Guar Hydroxypropyltrimonium Chloride, examples of which include polymers known via the INCI nomenclature as Hydroxypropyl Guar Hydroxypropyltrimonium Chloride, such as the products sold under the name Jagaur C-162 by the company Rhodia.

Suitable nonionic thickeners have the INCI names SPEG-180/Laureth-50 TMMG Copolymer, Butylene Glycol and Polyether-1 and are available from Rockwood under the brand name Pure Thix.

Suitable hydrophobically-modified polyacrylate polymers include: acrylates/C10-C30 alkylacrylates copolymers such as Ultrez® 20/21 from Lubrizol, and Permulen® TR1 from Lubrizol; acrylates/beheneth-25 methacrylate copolymers such as Aculyn® 28 from Rohm & Haas; acrylates/ceteth-20 itaconate copolymers such as Structure® 3001 or 2001 from Akzo Nobel.

Suitable associative thickeners include polyurethane-based polymers such as polyurethane-30, e.g. Luvigel-STAR® from BASF. Also EO-PO-block copolymers may be useful, for example Pluronics® from BASF. Further, urethane thickeners named Dermothix™ available from Alzo International Inc.

The viscosity-increasing agent may also be a polysaccharide, preferably at least one heteropolysaccharide. Suitable polysaccharides and heterosaccharides include starches and derivatives thereof, e.g. mono- or di-esters with phosphoric acid, cellulose types and their derivatives, xanthan gums, carrageenans. Preferred heteropolysaccharides include xanthan gum such as Keltrol® T from Kelco, and Natrosol®

250 HHR from Herkules. A preferred starch is hydroxypropyl starch phosphate such as Structure® XL from National Starch.

Further, thermosensitive polymers which are widely unaffected by pH such as Bis-methoxy PEG-13 PEG-438/PPG-1 10 SMDI copolymer (ExpertGel® EG 56), Bis-methoxy PEG-13 PEG-502/PPG-57/SMDI copolymer (ExpertGel® EG 230) or a mixture thereof; these polymers are available from PolymerExpert.

The viscosity-increasing agents may be present in the composition in an amount of from about 0.1% to about 10%, preferably about 0.2% to about 5.0%, by total weight of the composition.

The composition according to the invention can also contain silicones to set certain properties. Suitable compounds are, for example, the products sold by Dow Corning under the names Dow Corning® 556 Cosmetic Fluid (INCI name: Phenyl Trimethicone), DC 190 (INCI name: PEG/PPG-18/18 Dimethicone), DC 193 (INCI name: PEG-12 Dimethicone), DC 200, DC 1401 (INCI name: Cyclomethicone, Dimethiconol) and DC 1403 (INCI name: Dimethicone, Dimethiconol), and the commercial products DC 244, DC 344 and DC 345 (INCI name for each: Cyclomethicone) from Dow Corning, Q2-7224 (manufacturer: Dow Corning; a stabilized trimethylsilylamodimethicone, Dow Corning 929 emulsion (comprising a hydroxyamino-modified silicone, which is also referred to as amodimethicone), SM-2059 (manufacturer: General Electric), SLM-55067 (manufacturer: Wacker), and Abil Quat 3270 and 3272 (manufacturer: Th. Goldschmidt; diquaternary polydimethylsiloxanes, INCI name: Quaternium-80).

The silicones are preferably present in amounts of from 0.1 to 5.0% by weight, more preferably from 0.3 to 2.5% by weight, based on the weight of the composition.

Suitable fatty oils in preparations according to the invention can be animal or preferably vegetable oils, such as sweet almond oil, argan oil, avocado oil, calophyllum oil, lanolin and derivatives thereof, castor oil, sesame oil, olive oil, jojoba oil, babassu oil, shea butter liquid, linseed oil, sunflower oil; mineral oils whose distillation start point under atmospheric pressure is at about 250° C. and whose distillation end point is at 410° C., such as, for example, vaseline oil; esters of saturated or unsaturated fatty acids, such as alkyl myristates, e.g. isopropyl, butyl or cetyl myristate, hexadecyl stearate, ethyl or isopropyl palmitate, octanoic or decanoic triglycerides and cetyl ricinoleate.

Fatty oils and silicone oils can be used in amounts of from 0.1 to 5.0% by weight, preferably in amounts of from 0.1 to 1.0% by weight.

The compositions of the invention can also comprise opacifiers such as ammonium styrene/acrylates copolymer, DEA-styrene/acrylates/DVB copolymer, guanine, Mica, styrene/acrylamide copolymer, styrene/acrylates copolymer, styrene/DVB copolymer; opacifiers having a viscosity controlling role such as behenamide, erucamide, Nylon-12, Nylon-66, oleamide, oleyl palmitamide, stearamide, stearamide DEA-distearate, stearamide DIBA-distearate, stearyl erucamide.

These components can be used in amounts of from 0.1 to 3.0% by weight, preferably in amounts of from 0.1 to 1.0% by weight.

In addition, the compositions of the invention can comprise quaternary viscosity controlling agents. Examples are guar hydroxypropyltrimonium chloride, quaternium-18 bentonite, quaternium-18/benzalkonium bentonite, quaternium M-18 hectorite, TEA-hydrochloride.

The compositions of the invention may contain one or more thickening agents, preferably in amounts from about 0.05% to about 5%, preferably from about 0.1% to about 1%, by weight of the composition.

The compositions of the invention can also comprise protein hydrolyzates, such as animal protein hydrolyzates which are, for example, the protein hydrolyzates of elastin, keratin, silk and milk protein, which may also be in form of salts. Such products are on the market, for example, under the trade names of Dehylan® (Cognis), Promois® (Seiwa Kasei Co. Ltd.), Collapuron® (Cognis), Nutrilan® (Cognis), Gelita-Sol® (Deutsche Gelatine Fabriken Stoess & Co), Lexein® (Inolex) and Kerasol® (Croda).

According to the invention, the protein hydrolyzates may also be of vegetable origin, e.g. soybean, almond, pea, potato and wheat protein hydrolyzates are preferred. Such products are available for example, under the trade names Gluadin® (Cognis), DiaMin® (Diamalt), Lexein® (Inolex), Hydrosoy® (Croda), Hydrolupin® (Croda), Hydrosesame® (Croda), Hydrotritium® (Croda) and Crotein® (Croda).

The protein hydrolyzates or derivatives thereof are present in the preparations preferably in amounts of from 0.1 to 10% by weight, based on the total preparation. Amounts of from 0.1 to 2.5% by weight are particularly preferred.

Complexing agents may be selected from chelating agents, sequestering agents and salts of any of the foregoing. Examples of common chelating agents include ethylenediamine tetraacetic acid (EDTA), nitrilotriacetic acid, ethylenegylcol-bis(β-amino-ethyl ether)-N,N-tetraacetic acid and ethylenediamine-N,N'-disuccinic acid (EDDS).

Levels of chelants or sequestering agents in the compositions can be as low as about 0.05%, preferably 0.3% for commonly used chelants such as EDTA. EDDS for example will be more preferably used at levels of at least about 1%, even more preferably above about 2% by weight of the composition.

The pH of the compositions of the invention is acidic, preferably below the isoelectric point of human hair. The most preferred pH range is between 3.0 and 0.5.

According to another embodiment, the invention provides a method for reshaping keratinous fibers, in particular smoothing keratin fibers, in which:

(i) the hair is cleaned by washing with a clarifying shampoo and blow-dried;

(ii) an aqueous ready-to-use composition of the current invention containing glyoxylic acid or a glyoxyloyl amino acid and at least one dye is applied to the fibers and tack-dried, whereby the processing time is between 5 minutes and 45 minutes (iii) the fibers are shaped with the help of shaping aids with heating of the fibers;

(iv) fibers are rinsed out and towel-dried, then treated with an after-treatment product containing care ingredients.

Shaping aids for the purposes of the method according to the invention may be aids for mechanical reshaping, such as a heat-resistant comb or a brush, or a heatable smoothing or curling iron. The part of the iron that contacts hair may have different shapes. For instance, it may be chosen from a flat plates to straighten ("flat iron") or curved plates to curl hair. An helmet can also be used to provide the heat treatment.

"Heating" refers to the use of elevated temperature. In one embodiment, the heating is provided by directly contacting the keratinous fibers with a heat source, e.g., by heat styling of the keratinous fibers.

It is preferred for the heat treatment to take place in the style of smoothing using appropriately heated flat or curved plates, in particular metal or ceramic plates, by pressing the plate onto the fiber to be smoothed and moving the plate pressed onto the fiber along the fiber. The smoothing iron is preferably moved uniformly from the scalp along the hair fibers to the hair tips. This movement results in a mechanical reshaping of the fibers and coloring. In case straight hair should be curled a mechanical shaping aid such as the fully automated curling machine BaBylyssPro™ Miracurl or Revolution Bellissima™ from IMETEC are very useful. Alternatively, a manual MARK HILL Tiger Oh So Glam Wonder Waver may be used for smoothing waves instantly.

In another embodiment, the composition comprising glyoxylic acid and at least one dye is filled into a flat iron type which is able to transport the liquid to the hot plates, e.g. by a mechanical pump, where the liquid is brought in contact with the hair in an amount suitable for simultaneous reshaping and dyeing. US20120272993 discloses an appropriate iron type.

Raising the temperature of the hair by applying an iron to the hair wherein the iron temperature is at least 60° C., for example from 60 to 250° C., and further for example from 150 to 240° C., especially preferred is a temperature range from 180 to 230° C.; this step taking place before rinsing the composition from the hair.

In addition to the mechanical shaping aid according to the current invention another shaping aid may be a cosmetic composition which works as a lubricant and which is optionally applied, e.g. if the hair is in poor condition and it is not possible to gently glide the iron on the hair fibers; the application of the composition ensures that the iron can glide on the hair fairly easily and local over heating of the hair by unexpected stopping is avoided. Such compositions normally contain silicones which are widely heat resistant in the applied temperature range.

The compositions and methods of the present invention provide a novel way to effectively reshaping and coloring the hair without significantly damaging the fibers.

Notwithstanding that the numerical ranges and parameters setting forth the broad scope of the invention are approximations, the numerical values set forth in the specific examples are reported as precisely as possible. The following examples are intended to illustrate the invention without limiting the scope as a result. The percentages are given on a weight basis.

EXAMPLES

Prior to the application of the compositions of the following examples, hair was washed with a deep cleansing shampoo and dried.

Trials on the head were performed by well trained experts familiar with reshaping procedures and assessments.

Example 1

A standard composition was used for the preparation of the reshaping and coloring agent. In the current example only dyes and amount of dyes were varied. The amounts of dyes used for the preparation of the reshaping and coloring composition are indicated in Table 1 for the anionic dyes, in Table 2 for the cationic dyes and in Table 3 for the nonionic dyes.

| Cosmetic composition for simultaneous reshaping and coloring hair | |
|---|---|
| Glyoxylic acid, 50% in water | 35.00% |
| Propylene glycol | 40.00% |
| Bis-PEG/PPG-20/20 Dimethicone | 1.50% |
| Cetrimonium chloride | 0.75% |
| Guar hydroxypropyltrimonium chloride | 0.30% |
| Disodium EDTA | 0.10% |
| Dyes and amounts | indicated in Table 1 |
| Water | ad 100.00% |

| Example | Dye | Amount | Color [RAL] | Intensity |
|---|---|---|---|---|
| Table 1-1: Acid Dyes, Amounts and Color Results | | | | |
| 1-1.1 | Acid Yellow 3 | 0.25% | 1016 sulfur yellow | medium |
| 1-1.2 | Acid Yellow 23 | 0.25% | 1021 rape yellow | very strong |
| 1-1.3 | Acid Yellow 1 | 0.20% | 1018 zinc yellow | medium-strong |
| 1-1.4 | Acid Red 92 | 0.20% | 3015 light pink | medium |
| 1-1.5 | Acid Red 52 | 0.60% | 4010 telemagenta | strong |
| 1-1.6 | Acid Red 40 | 0.40% | 2012 salmon orange | medium-strong |
| 1-1.7 | Acid Red 33 | 0.50% | 4003 heather violet | weak-medium |
| 1-1.8 | Acid Red 18 | 0.25% | 2012 salmon orange | medium |
| 1-1.9 | Acid Orange 7 | 0.50% | 2011 deep orange | weak-medium |
| 1-1.10 | Acid Violet 43 | 0.50% | 5023 distant blue | strong |
| 1-1.11 | Acid Green 25 | 0.30% | 6033 mint turquoise | medium |
| 1-1.12 | Acid Blue 9 | 0.25% | 5018 turquoise blue | medium |
| 1-1.13 | Acid Blue 7 | 1.00% | 5021 water blue | very strong |
| 1-1.14 | Acid Black 1 | 0.25% | 7033 cement grey | medium |
| Table 1-2: Cationic Dyes, Amounts and Color Results | | | | |
| 1-2.1 | Basic Yellow 87 | 0.50% | 1016 sulfur yellow | very strong |
| 1-2.2 | Basic Yellow 57 | 0.50% | 1018 zinc yellow | strong |
| 1-2.3 | Basic Violet 2 | 0.10% | 4001 red lilac | medium |
| 1-2.4 | Basic Red 76 | 1.00% | 2012 salmon orange | medium |
| 1-2.5 | Basic Red 51 | 0.50% | 3017 rose | medium-strong |
| 1-2.6 | Basic Orange 69 | 1.00% | 1034 pastel yellow | medium |
| 1-2.7 | Basic Orange 31 | 0.50% | 2001 red orange | medium |
| 1-2.8 | Basic Brown 17 | 1.00% | 8023 orange brown | medium-strong |
| 1-2.9 | Basic Blue 99 | 0.50% | 7036 platinum grey | medium |
| 1-2.10 | HC Blue 15 | 0.50% | 5017 traffic blue | strong |

-continued

| Example | Dye | Amount | Color [RAL] | Intensity |
|---|---|---|---|---|
| | Table 1-3: Non Ionic Dyes, Amounts and Color Results | | | |
| 1-3.1 | HC Yellow 7 | 0.13% | 1002 sand yellow | medium |
| 1-3.2 | HC Yellow 13 | 1% | 1016 sulfur yellow | strong |
| 1-3.3 | HC Orange NO. 1 | 0.50% | 1033 dahlia yellow | strong |
| 1-3.4 | Disperse Blue 377 | 0.50% | 6021 pale green | weak |
| 1-3.5 | Disperse Black 9 | 0.15% | 1012 lemon yellow | strong |
| 1-3.6 | Disperse Violet 1 | 0.25% | 4005 blue lilac | medium |
| 1-3.7 | 4-Nitro-o-phenylenediamine | 0.25% | 1012 lemon yellow | medium |
| 1-3.8 | 2-Amino-6-chloro-4-nitrophenol | 0.50% | 2009 traffic orange | strong |

The compositions comprising the dyes were applied to light blond Brazilian hair which was curly to frizzy. Then the hair was tack-dried by means of a blow dryer. Tack-dried hair has an average humidity of 30-40%. The compositions were left on the hair for 20 minutes. A detangling cream is applied to the hair and distributed evenly using a comb. Without rinsing off, the hair is brushed followed by straightening by means of a flat iron (220° C., 10 cycles). The hair was then washed and a rehydrating mask is applied to the hair, left for 5 min and rinsed off. The hair is dried with a hair dryer. The previously curly hair was well straightened and colored in the above indicated colors.

A high relaxation efficiency after 24 hours under 90% relative humidity indicates that the hair did not display reversion. The data show that naturally curly Brazilian hair can be effectively straightened and simultaneously colored without substantial reversion after being treated with solutions containing the inventive composition.

Example 2

The following composition is prepared and 60 ml thereof are filled into a squeeze foamer or a pump foamer.

TABLE 2-1

| Ingredient (INCI) | Amount |
|---|---|
| Glyoxylic acid 50% in water | 35.00% |
| Propylene glycol | 5.00% |
| Cetrimonium chloride | 0.50% |
| Coceth-7 | 0.48% |
| PPG-1-PEG-9 Lauryl glycol ether | 0.36% |
| PEG-40 Hydrogenated Castor oil | 0.24% |
| PEG-15 Cocopolyamine | 0.50% |
| Perfume | 0.60% |
| Disodium EDTA | 0.10% |
| Acid Violet 43 | 1.50% |
| Water | ad 100.00% |

The foam is applied to washed human hair, tack-dried by means of a blow dryer and left on the hair for 20 minutes.

Straightening and Coloring Hair

A section of about 5 cm width of mid-brown hair is placed between the 2 hot plates of the 230° C. pre-heated flat iron with the appliance positioned close to the roots. The hair is held firmly with the flat iron, then the iron is moved slowly along from the roots to the tips. This procedure is repeated until the hair is well straightened.

Curling and Coloring Hair

In this case the untreated hair is flat and the selected device for reshaping is BaBylissPRO MiraCurl™ or Revolution Bellissima from IMETEC.

Straight mid-brown hair is treated with the ready-to-use composition as described. Following the instructions of the device, the pre-heated styler is positioned close to the roots, the selected hair section is inserted, then the device is closed. The hair is pulled into the device, heated and held according to the settings, e.g. at 230° C. for a time of between 5 to 15 seconds. The styling device is removed.

After straightening or curling the hair as described above, the hair is washed and a rehydrating mask is applied to the hair, left about 5 minutes and rinsed off The hair is dried with a hair dryer.

In both cases the mid-brown hair is reshaped and very shiny with strong violet reflexes.

Example 3

A cosmetic composition according to example 1 was used whereas in example 3 more than one dye of the same and also of different ionogenic nature were used. The amounts of the dyes and the obtained color results are indicated in table 3-1. Processing was performed as described in example 1.

TABLE 3-1

Combinations of dyes with the same and of different ionogenic nature in a composition for simultaneous coloring and reshaping

| Dye | Ionogenic nature | Examples [dyes in % by weight of the ready-to-use mixture] | | | | | | | | | | | |
|---|---|---|---|---|---|---|---|---|---|---|---|---|---|
| | | 3-1.1 | 3-1.2 | 3-1.3 | 3-1.4 | 3-1.5 | 3-1.6 | 3-1.7 | 3-1.8 | 3-1.9 | 3-1.10 | 3-1.11 | 3-1.12 |
| Acid Black 1 | anionic | | | | | | | | | | | 0.028 | |
| Acid Blue 7 | anionic | 0.111 | | | | | | | | | | | |
| Acid Blue 9 | anionic | 0.056 | | | | | 0.111 | | | | | | |
| Acid Green 25 | anionic | | | | | | | | | | | | 0.038 |
| Acid Orange 7 | anionic | | | | | | | | | | | | 0.042 |
| Acid Red 18 | anionic | | | | | | | | | | | | |
| Acid Red 33 | anionic | | | | | | 0.045 | | | | 0.114 | | |
| Acid Red 40 | anionic | 0.044 | | | | | | | | | | 0.089 | |

TABLE 3-1-continued

Combinations of dyes with the same and of different ionogenic nature in a composition for simultaneous coloring and reshaping

| Dye | Ionogenic nature | 3-1.1 | 3-1.2 | 3-1.3 | 3-1.4 | 3-1.5 | 3-1.6 | 3-1.7 | 3-1.8 | 3-1.9 | 3-1.10 | 3-1.11 | 3-1.12 |
|---|---|---|---|---|---|---|---|---|---|---|---|---|---|
| Acid Red 52 | anionic | | | 0.086 | | | | 0.100 | | | | | |
| Acid Red 92 | anionic | 0.022 | | | | | | | | | | | |
| Acid Yellow 1 | anionic | | | 0.043 | | | 0.018 | | | | | | |
| Acid Yellow 23 | anionic | | | | | | | | | | 0.068 | | |
| Acid Yellow 3 | anionic | 0.056 | | | | | | | | | | | |
| Tetrabromophenol Blue | anionic | | | | | | | | | | 0.036 | | |
| Basic Orange 31 | cationic | | | | | | | | | | | 0.111 | |
| Basic Red 51 | cationic | | | | 0.100 | 0.200 | | | | | | | 0.125 |
| Basic Red 76 | cationic | | | | | | | | 0.208 | | | | |
| Basic Violet 2 | cationic | | | | | | | | | | | 0.022 | |
| Basic Yellow 57 | cationic | | | | | | | | | | | | 0.021 |
| Basic Yellow 87 | cationic | | | | | 0.200 | 0.091 | 0.111 | | | | | |
| HC Blue 15 | cationic | | | | 0.020 | 0.020 | | | | | 0.018 | | |
| Ext. D&C Violet 2 | nonionic | | 0.125 | 0.071 | | | 0.045 | | | | | | |
| Disperse Black 9 | nonionic | | | | | | | | | 0.025 | | | |
| Disperse Blue 377 | nonionic | | | | | | | | | 0.208 | | | |
| HC Yellow 7 | nonionic | | 0.031 | | | | | | | | 0.045 | | |
| 4-Amino-3-nitrophenol | nonionic | | 0.125 | | 0.300 | | | | | | | | |
| 2-Amino-6-chloro-4-nitrophenol | nonionic | | | | | | | | | | 0.182 | | 0.125 |
| Color [RAL] | | 6021 pale green | 7002 olive grey | 3014 antique pink | 7006 beige grey | 7036 platinum grey | 1001 beige | 7036 platinum grey | 1015 light ivory | 6018 yellow green | 6021 pale green | 3017 rose | 3012 beige red |

The results of example 3 demonstrate the high compatibility of the cosmetic carrier system with dye combinations of the same or of different ionogenic nature and glyoxylic acid for simultaneous coloring and reshaping.

The previously curly light blond hair was well straightened and shiny and, after the treatment, showed the reflexes as indicated in Table 3-1.

Example 4

A cosmetic composition according was used whereas a variety of straightening ingredients were used. Processing was performed as described in example 1.

TABLE 4.1

Straightening compositions comprising various active straightening ingredients and a dye

| Ingredient (INCI) | Amount | Amount |
|---|---|---|
| Glyoxylic acid | — | 8.75% |
| Glyoxyloyl Carbocysteine | 10.00% | 5.00% |
| Glyoxyloyl Keratin Amino Acids | 6.00% | 5.00% |
| Propylene Glycol | 5.00% | 5.00% |
| Cetrimonium Chloride | 0.75% | 0.75% |
| Acid Red 52 | 0.60% | 0.60% |
| Guar Hydroxypropyltrimonium Chloride | 0.30% | 0.30% |
| Disodium EDTA | 0.10% | 0.10% |
| Water | ad 100.00% | ad 100.00% |

The pH of the compositions was 1.6. In both cases the previously light blond Brazilian hair which was curly to frizzy was colored in pink and the hair was well straightened.

Example 5

The composition of this example was tested on 12 Brazilian models having different hair qualities from curly to more frizzy mid blond hair. As usually hair was washed by using a deep cleansing shampoo and dried with a blow-dryer. Then the reshaping and coloring composition was applied, tack-dried and left on the hair for 35 minutes.

| Ingredient (INCI) | Amount |
|---|---|
| Glyoxylic Acid 50% | 35.0% |
| Propylene glycol | 5.0% |
| Cetyltrimethylammonium chloride | 3.0% |
| Guar hydroxypropyltrimonium chloride | 0.3% |
| Quaternised hydrolysed collagen protein | 0.3% |
| ABIL B 8832 (from Evonik) | 1.5% |
| Antara 430 (from ISP) | 0.6% |
| Promois WK-HSIGH | 0.2% |
| Polysorbate 20 | 0.2% |
| Babassu oil | 0.1% |
| Disodium EDTA | 0.1% |
| Acid Yellow 23 | 0.73% |
| FD&C Red 40 | 0.68% |
| Acid Blue 7 | 0.23% |
| 2-Amino-6-chloro-4-nitrophenol | 0.55% |
| Water | ad 100.0% |

Then strand by strand is smoothed as usually by using a flat iron heated to 190-220° C. for 10 times. After rinsing the hair and the application of a care composition and drying the hair was shiny, well straightened and colored in a medium brown shade.

The invention claimed is:

1. A ready-to-use composition for simultaneous reshaping and coloring of hair comprising at least one direct dye and a compound of formula (I) or the corresponding monohydrate of formula (II), respectively,

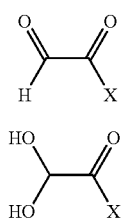

wherein X is either a hydroxy group, or X is a —NHR group wherein R represents an amino acid residue and the N atom is the amino group of the corresponding amino acid, said compounds of formula I or II being present in a concentration from 5.5 to 25% by weight, and wherein said composition is characterized by a pH between 0.5 and 3.0.

2. A composition according to claim 1 wherein the compound of formula I or II is selected from glyoxylic acid or a glyoxyloyl amino acid.

3. A composition according to claim 1 wherein said at least one dye is selected from anionic, neutral or cationic dyes.

4. A composition according to claim 3 wherein said at least one dye is an anionic dye.

5. A composition according to claim 4 wherein said at least one dye is selected from Acid Yellow 1, Acid Yellow 3, Acid Yellow 23, Acid Orange 7, Acid Red 33, Acid Red 40, Acid Red 52, Acid Red 92, Acid Violet 43, Acid Blue 7 and Acid Blue 9.

6. A composition according to claim 3 wherein said at least one dye is a non ionic dye.

7. A composition according to claim 6 wherein said at least one dye is selected from HC Yellow No. 7, 2-Amino-6-chloro-4-nitrophenol, 4-Nitro-o-phenylenediamine, 4-Amino-3-nitrophenol, HC Orange No. 1, HC Red No. 1, HC Red No. 3, HC Red No. 13, Disperse Violet 1, HC Yellow No. 13 and Disperse Red 17.

8. A composition according to claim 3 wherein said at least one dye is a cationic dye.

9. A composition according to claim 8 wherein said at least one dye is selected from Basic Yellow 57, Basic Yellow 87, Basic Brown 16, Basic Brown 17, Basic Orange 31, Basic Red 51, Basic Red 76, HC Blue 15 and HC Blue 16, Basic blue 75 and Basic blue 124.

10. A composition according to claim 1 wherein the concentration of said at least one dye is between 0.01% and 5% by weight.

11. A composition according to claim 1 further comprising one or more auxiliary agents selected from anionic, neutral or cationic surfactants, anionic, neutral or cationic thickeners, organic solvents, silicones, cationic polymers.

12. A ready to use composition according to claim 1 obtained by mixing a first agent containing glyoxylic acid or a glyoxyloyl amino acid and a second agent containing at least one dye.

13. A kit for the preparation of a ready to use hair reshaping and coloring composition of claim 12 comprising a first agent containing glyoxylic acid or a glyoxyloyl amino acid and a second agent containing at least one dye.

14. A process for the reshaping and direct coloring of hair, comprising:
(i) contacting the hair with an aqueous ready-to-use composition according to claim 1 containing glyoxylic acid or a glyoxyloyl amino acid and a dye, whereby the processing time is between 5 minutes and 45 minutes;
(ii) shaping the hair by means of heat and shaping aids.

15. A process according to claim 14 further comprising pre-washing the hair and rinsing and drying steps before or after the shaping step (ii).

* * * * *